(12) United States Patent
Kalmann et al.

(10) Patent No.: US 9,155,618 B2
(45) Date of Patent: *Oct. 13, 2015

(54) DEVICE FOR REGULATING BLOOD

(75) Inventors: Menno Kalmann, Elspeet (NL); Peter W. J. Hinchliffe, Campbell Hall, NY (US); Adam I. Lehman, Northford, CT (US)

(73) Assignee: Deep Vein Medical, Inc., Canton, MA (US)

( * ) Notice: Subject to any disclaimer, the term of this patent is extended or adjusted under 35 U.S.C. 154(b) by 445 days.

This patent is subject to a terminal disclaimer.

(21) Appl. No.: 13/344,928

(22) Filed: Jan. 6, 2012

(65) Prior Publication Data

US 2012/0101568 A1    Apr. 26, 2012

Related U.S. Application Data

(63) Continuation of application No. 12/319,176, filed on Jan. 2, 2009, now Pat. No. 8,092,517, and a continuation-in-part of application No. 11/801,691, filed on May 10, 2007, now Pat. No. 7,811,316, and a continuation-in-part of application No. 11/801,489, filed on May 10, 2007, now abandoned.

(60) Provisional application No. 60/808,406, filed on May 25, 2006, provisional application No. 60/809,483, filed on May 31, 2006, provisional application No. 61/010,012, filed on Jan. 4, 2008.

(51) Int. Cl.
*A61F 2/82* (2013.01)
*A61F 2/24* (2006.01)

(52) U.S. Cl.
CPC .............. *A61F 2/2418* (2013.01); *A61F 2/2475* (2013.01); *A61F 2220/005* (2013.01); *A61F 2220/0058* (2013.01); *A61F 2230/0054* (2013.01)

(58) Field of Classification Search
CPC ........................................................ A61F 2/82
USPC ........................................ 623/2.1–2.19, 1.24
See application file for complete search history.

(56) References Cited

U.S. PATENT DOCUMENTS

| | | | | |
|---|---|---|---|---|
| 7,618,447 | B2 * | 11/2009 | Case et al. | 623/1.26 |
| 8,092,517 | B2 * | 1/2012 | Kalmann et al. | 623/1.24 |
| 8,109,993 | B2 * | 2/2012 | Hinchliffe et al. | 623/1.24 |
| 2004/0260389 | A1 * | 12/2004 | Case et al. | 623/1.24 |
| 2007/0050013 | A1 * | 3/2007 | Gross | 623/1.24 |
| 2009/0105813 | A1 * | 4/2009 | Chambers et al. | 623/2.12 |
| 2010/0168839 | A1 * | 7/2010 | Braido et al. | 623/1.26 |
| 2011/0213460 | A1 * | 9/2011 | Lashinski et al. | 623/2.18 |

* cited by examiner

*Primary Examiner* — Suzette J Gherbi
(74) *Attorney, Agent, or Firm* — Brown Rudnick LLP; Thomas C. Meyers

(57) ABSTRACT

An implantable device for regulating blood flow through a blood vessel comprising an elongated support dimensioned and configured to be implanted in a blood vessel. The support includes a linking member linking axially spaced apart portions to one another. A valve membrane extends between the axially spaced apart support portions and includes first region folded over the first linking member and attached thereto and a second region adjacent the first region and unattached to the first linking member. The second region is movable between a first position to enable blood flow and a second position to inhibit blood flow.

24 Claims, 10 Drawing Sheets

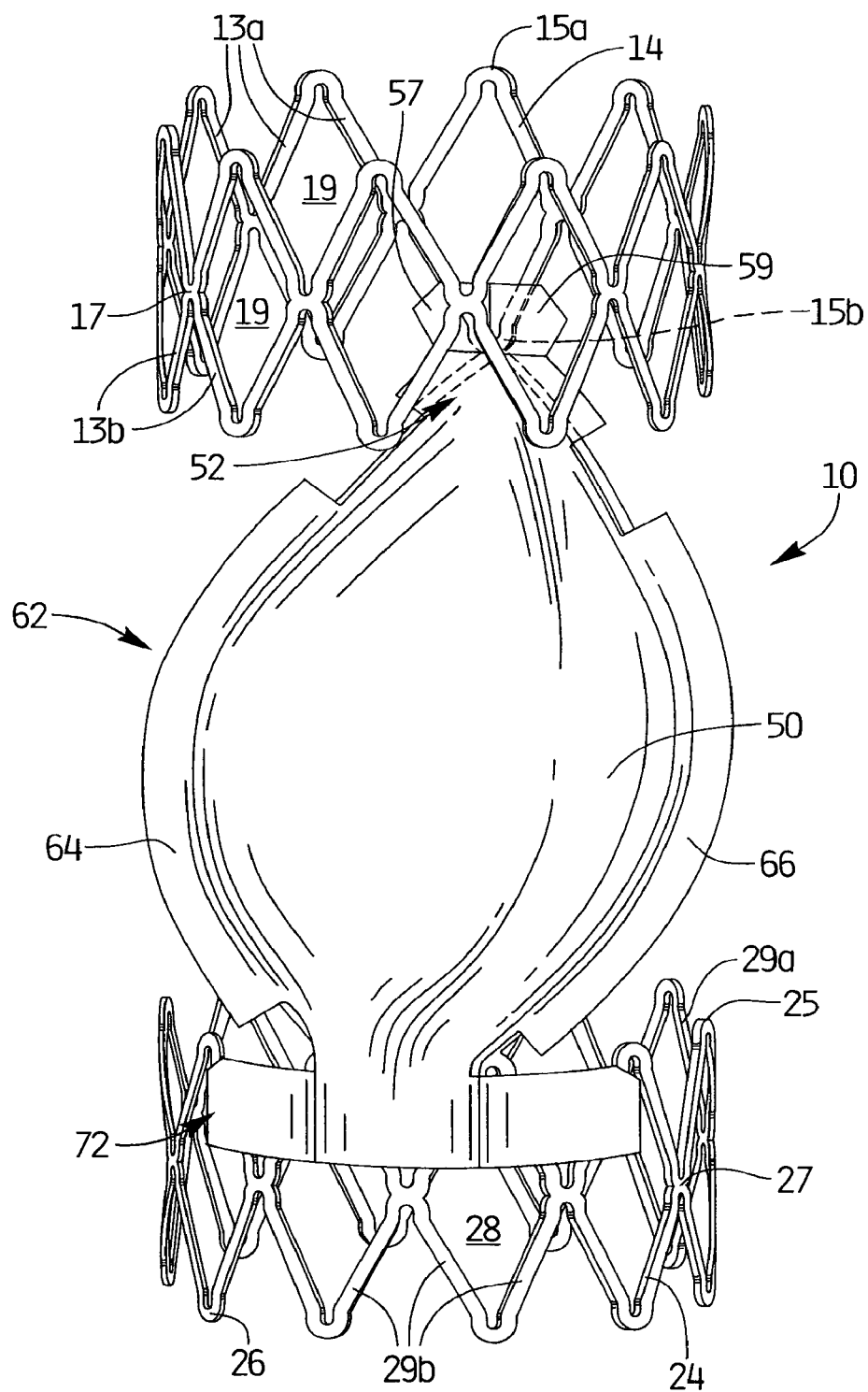
FIG_1

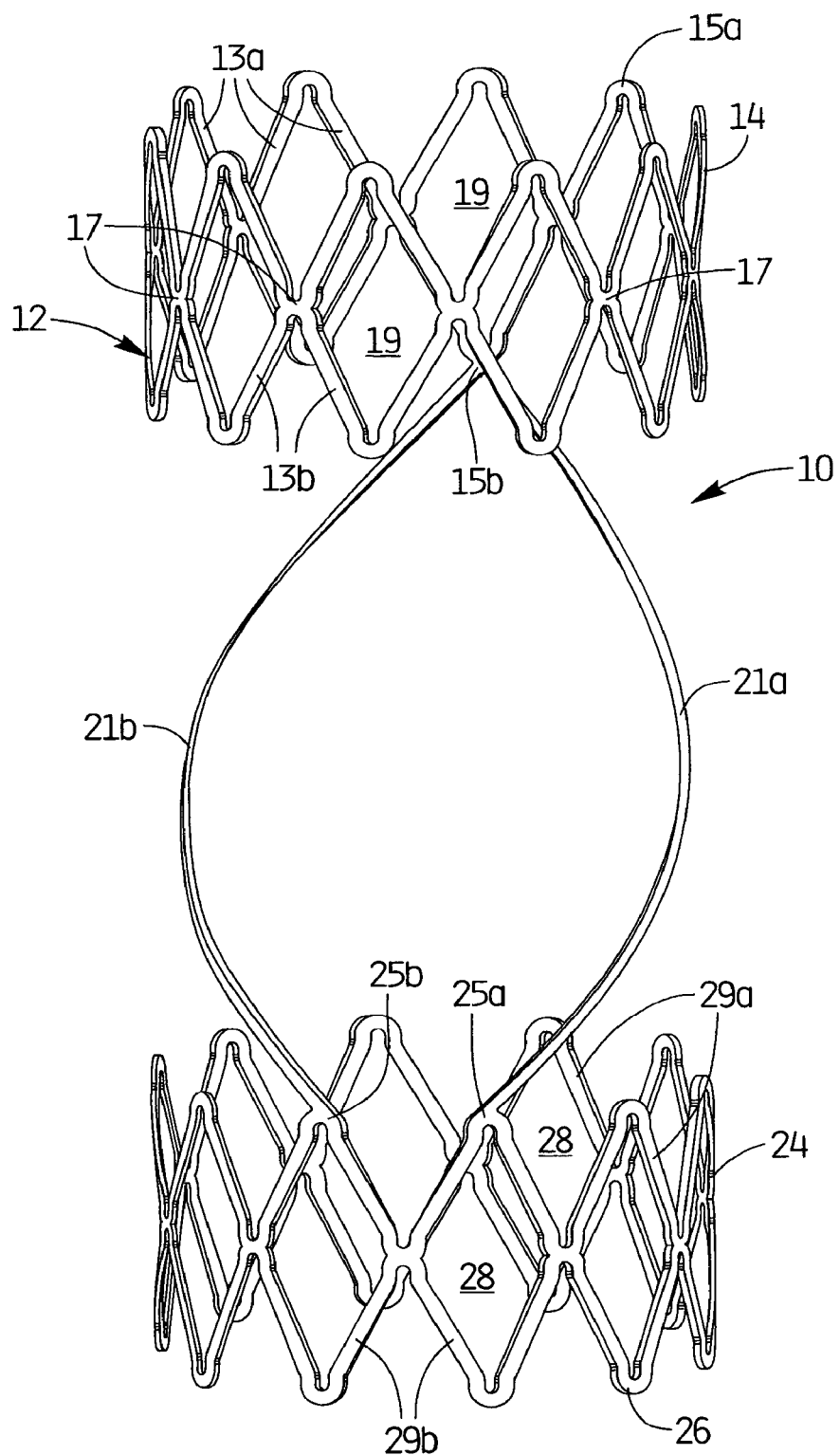
FIG_2

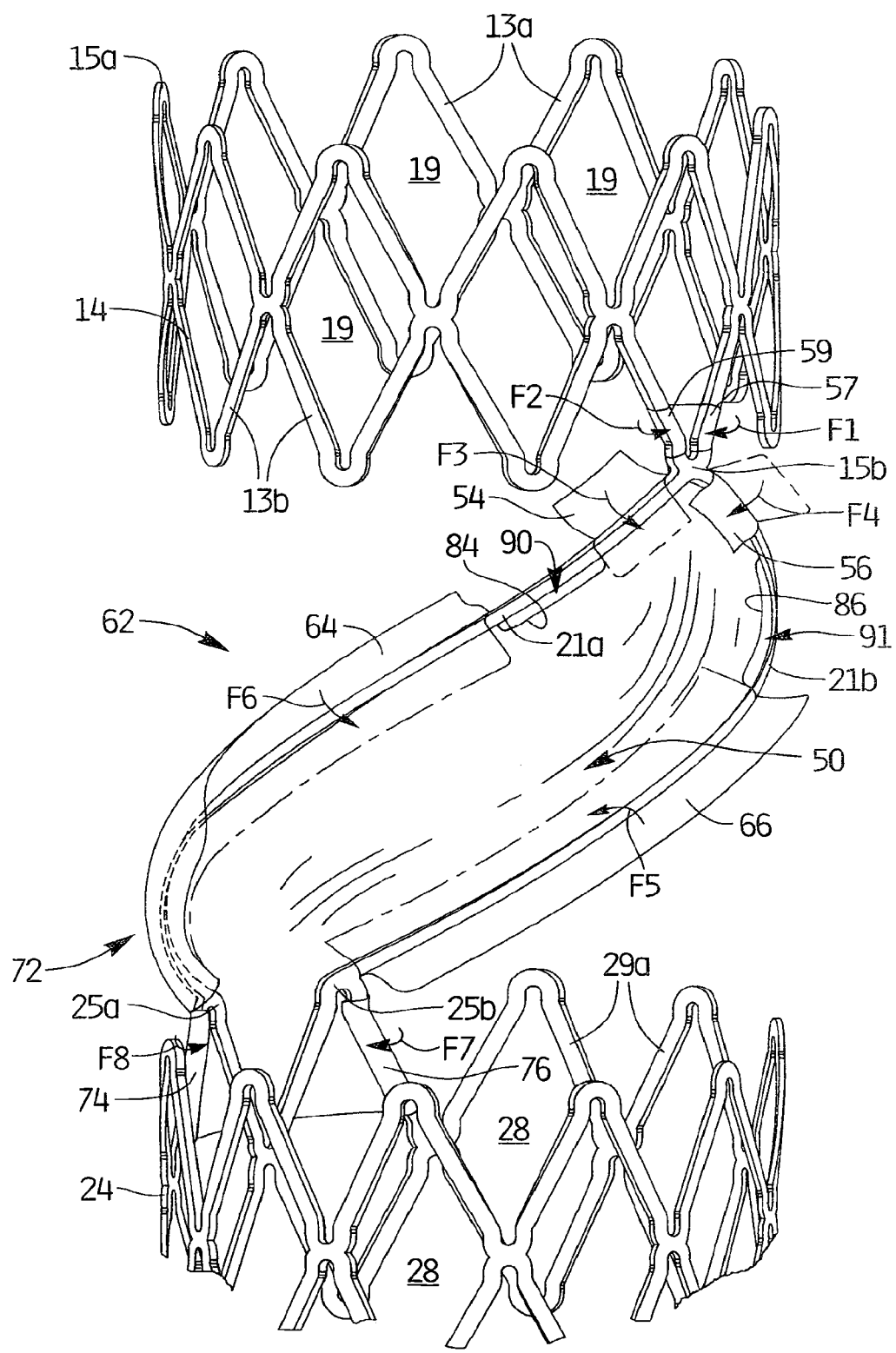
FIG_3

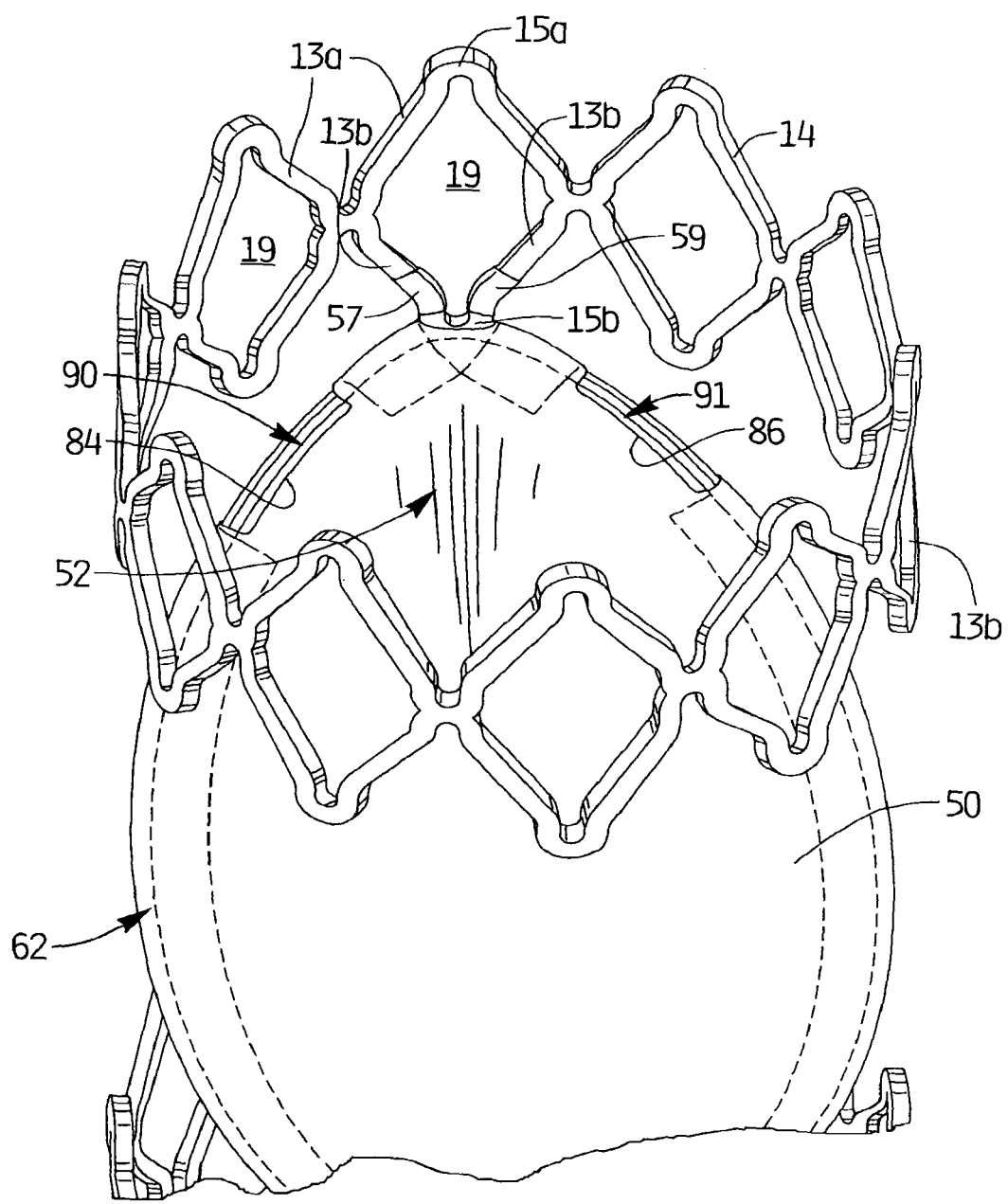
FIG_4

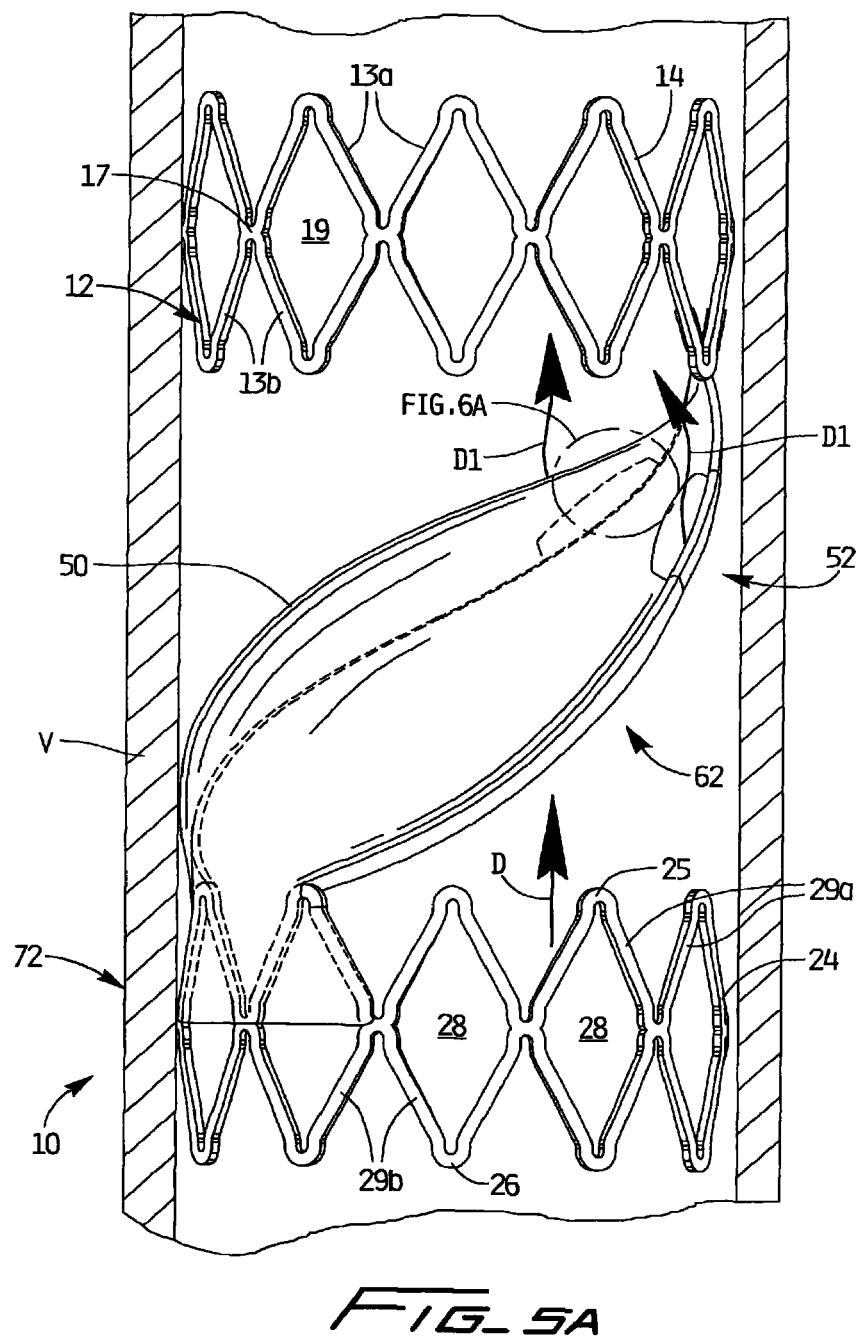
FIG_5A

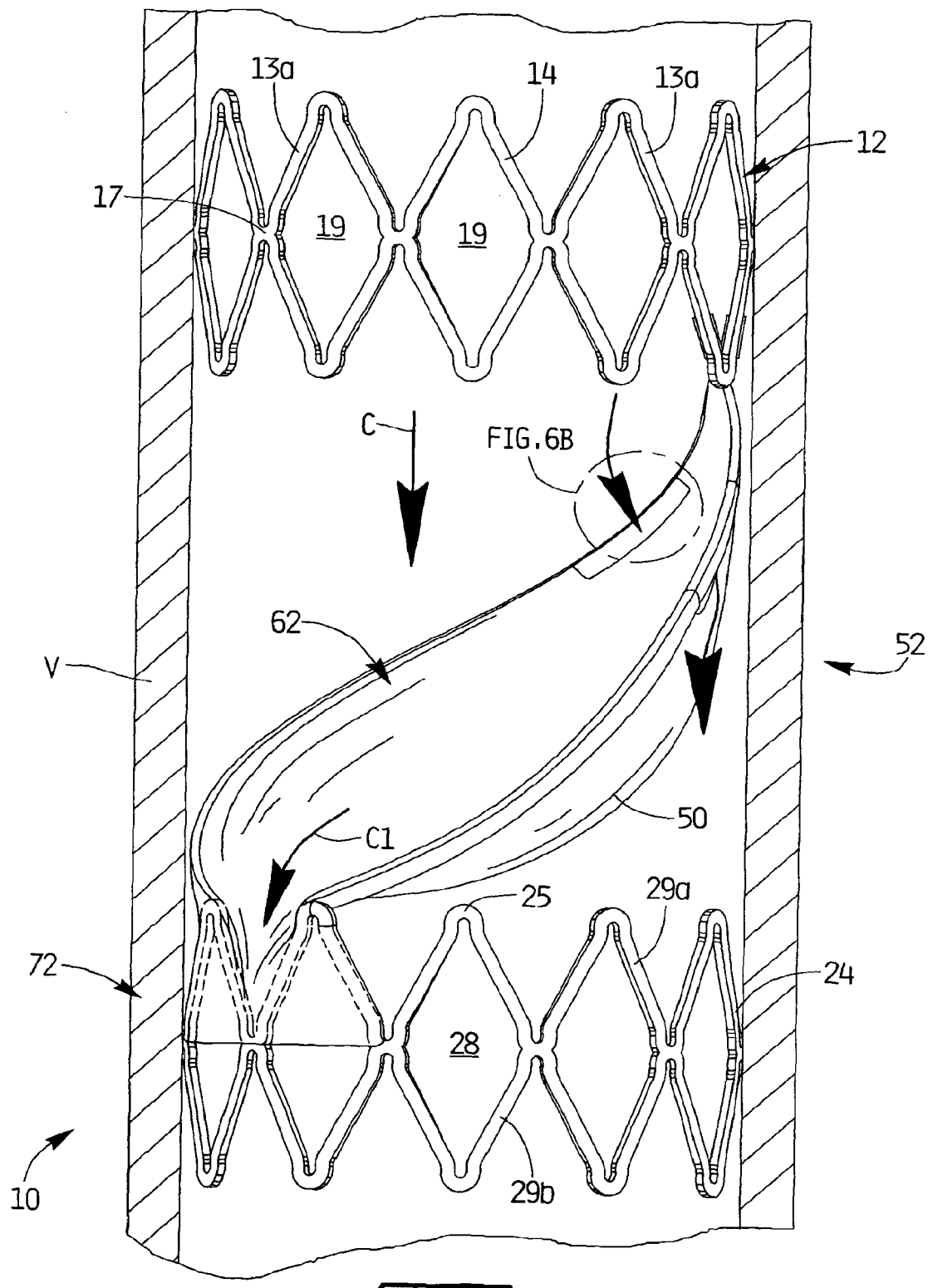
FIG_5B

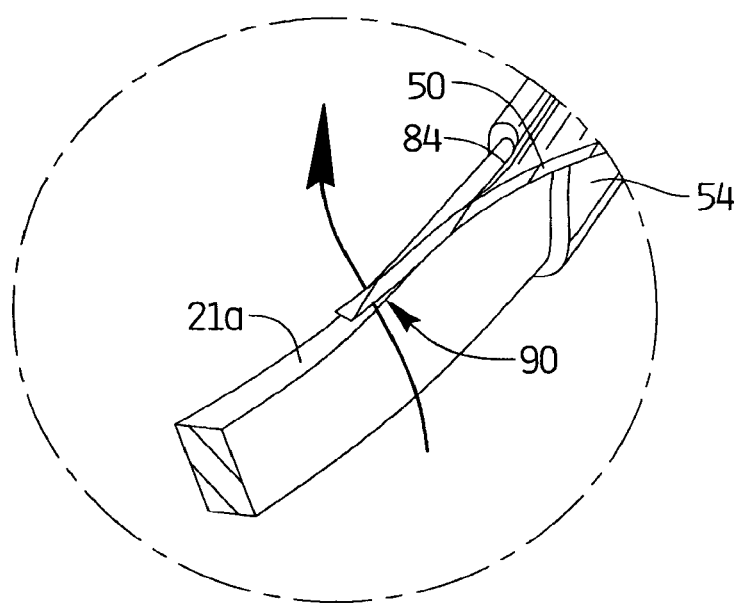
FIG_6A
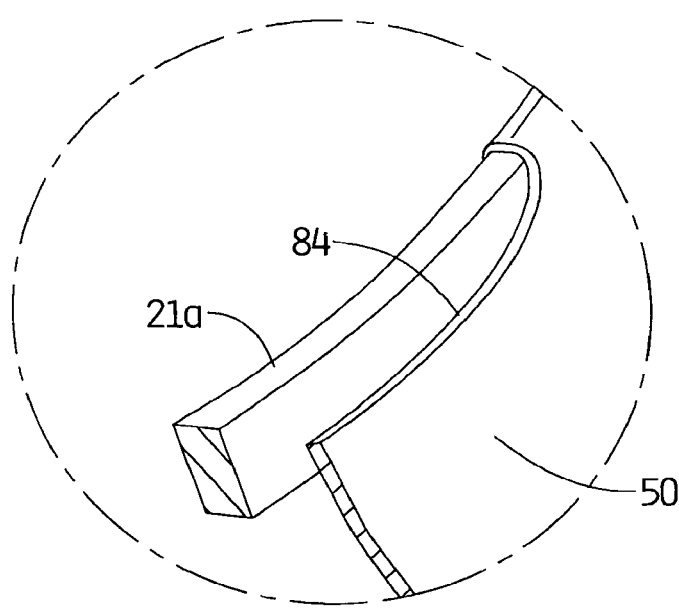
FIG_6B

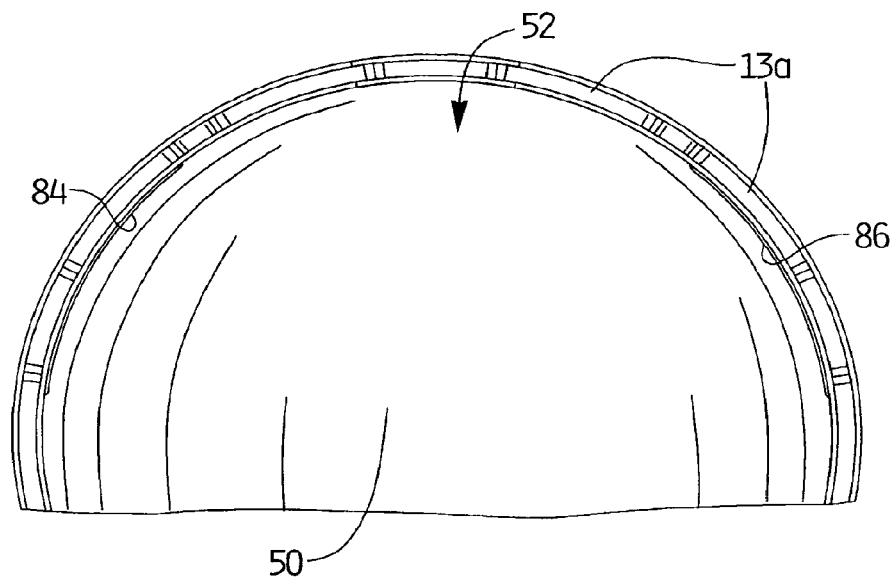
FIG_6C
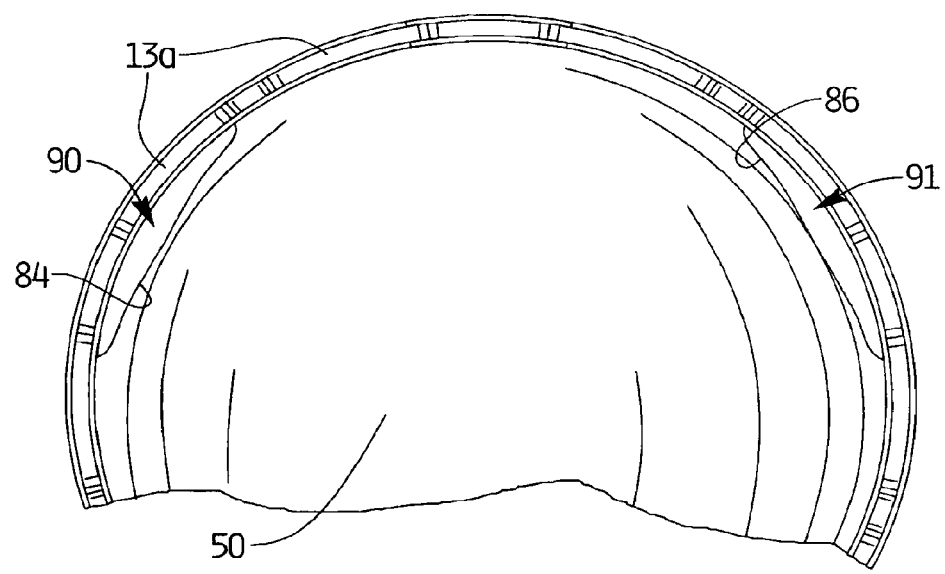
FIG_6D

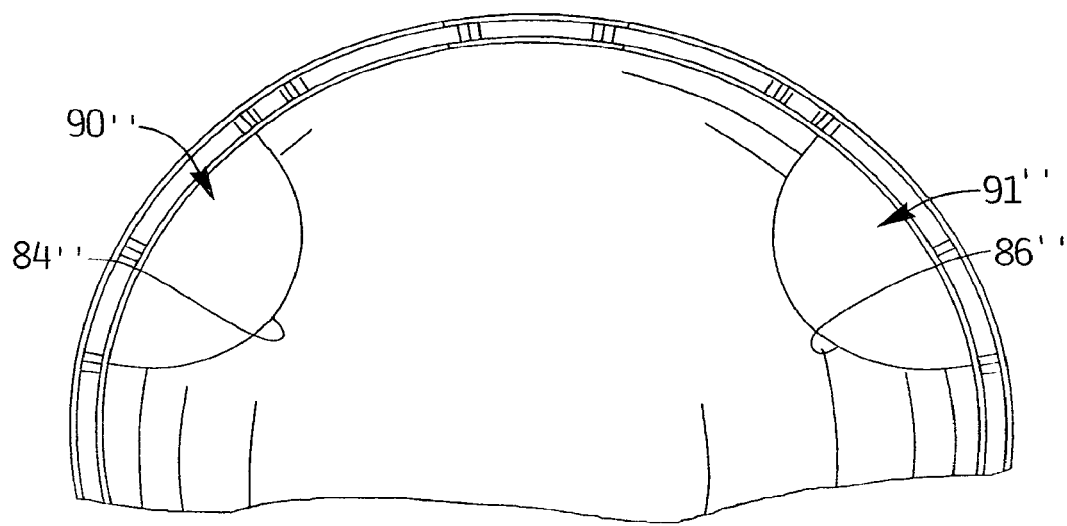
FIG_6E
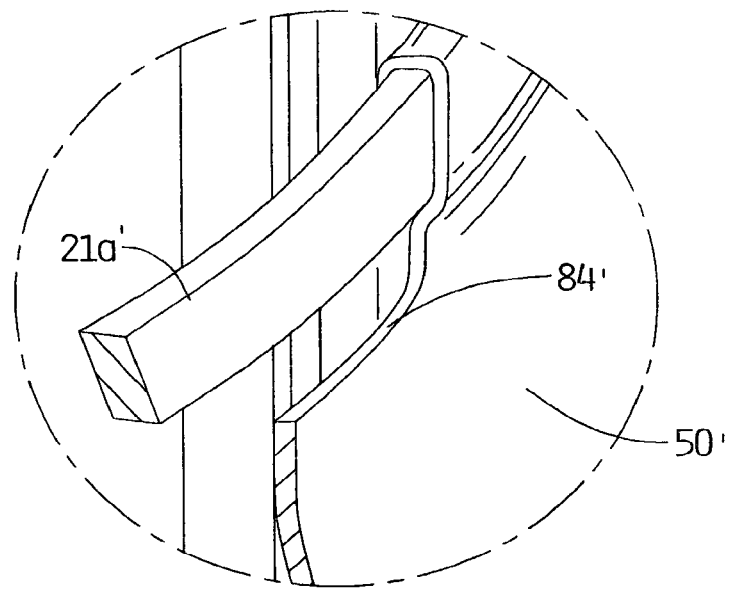
FIG_7A

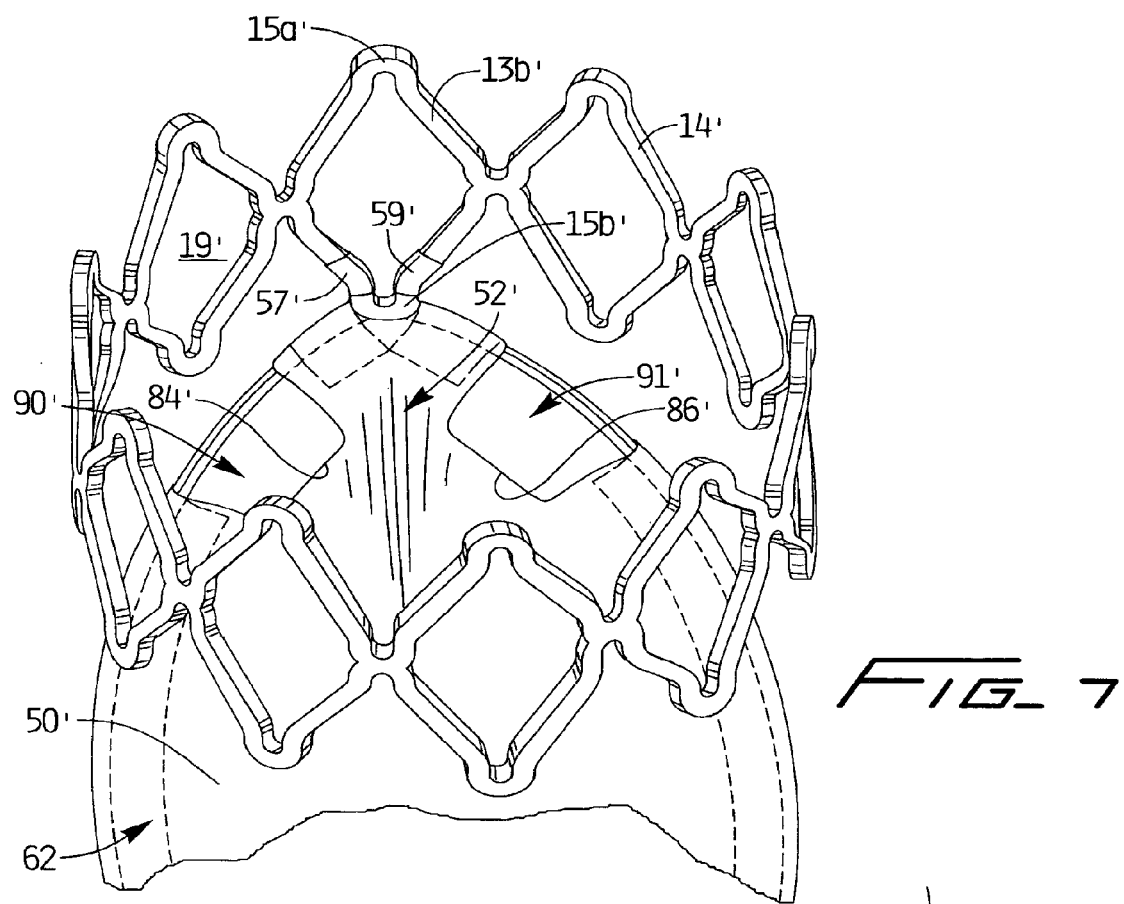
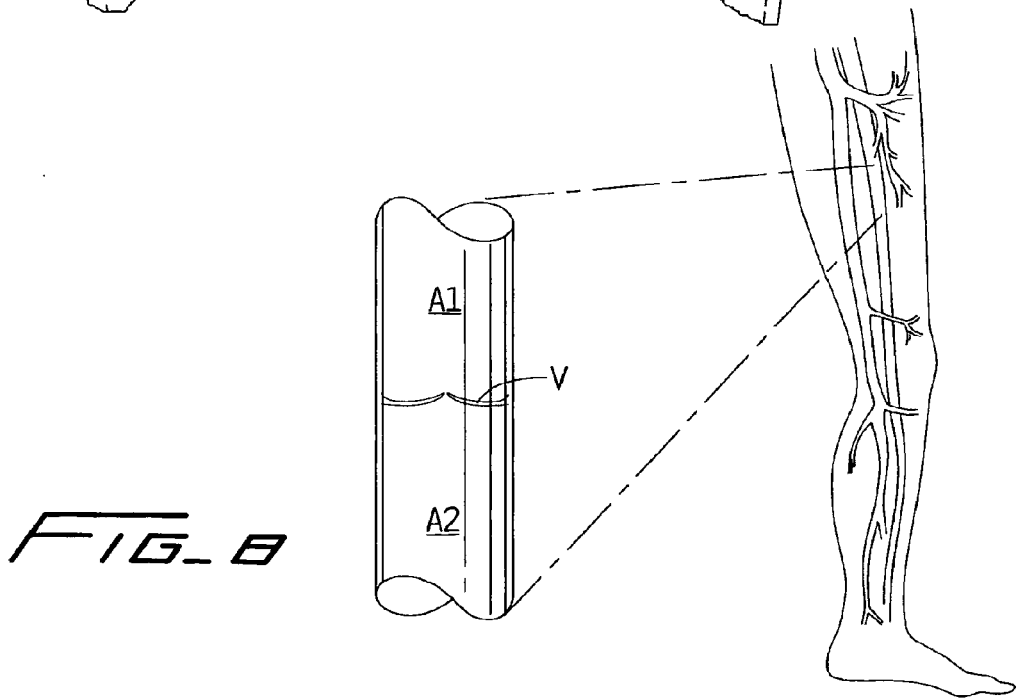

DEVICE FOR REGULATING BLOOD

CROSS-REFERENCE TO RELATED APPLICATIONS

This application is a continuation of U.S. application Ser. No. 12/319,176, filed on Jan. 2, 2009, which claims priority from U.S. provisional application Ser. No. 61/010,012 filed Jan. 4, 2008, and is a continuation-in-part of both U.S. application Ser. No. 11/801,489, filed May 10, 2007 and U.S. application Ser. No. 11/801,691, filed May 10, 2007 (now U.S. Pat. No. 7,811,316, each of which claim priority from U.S. provisional application Ser. Nos. 60/808,406, filed May 25, 2006, and 60/809,483, filed May 31, 2006. The contents of each of these application are incorporated herein by reference in their entireties.

FIELD OF THE INVENTION

The subject invention is directed to a device for regulating blood flow in the venous system, and more particularly, to an implantable valve device for regulating the flow of blood through a blood vessel.

DESCRIPTION OF RELATED ART

The blood system, and in particular the venous blood system of the legs and arms is provided with valves that are uniquely located in a manner so as to ensure that blood will not flow back upstream in the direction from which it has been pumped from the heart. In the arms and legs, there is a deep venous system and a surface (superficial) venous system. Due to various causes, thrombosis can occur in the deep venous system. Blood thinning can alleviate this problem. However, valves do not effectively close and often leak when the blood in thinned. This can cause increased venous blood pressure in the direction of the ankles, which can lead to a variety of problems including pain, swelling, varicose veins and ulcers. Complaints of this type are wide spread among those who spend prolonged periods of time in a standing position, for instance, surgeons.

The surface venous system of the leg is relatively weaker than the deep venous system, and it has the tendency to spontaneously widen due to the increased pressure of blood from above. This widening prevents the valves from functioning effectively and can lead to varicose veins, which are both unattractive and painful. Major surgery is often required to treat these blood vessel problems. For example, varicose veins are treated by either closing off the vein, which leads to a reduced blood flow capacity and increased pressure on surrounding blood vessels to ensure blood drainage, or by completely removing the varicose veins, which leads to the same problem. The deep veins require invasive surgery and because of the swelling, risk of infection and trauma is seldom attempted. In either case, the treatment of the surface veins does not treat the failed valves in the deep system, thereby causing the continued pressure and back flow into the legs. The subject invention is directed to a device for obviating problems of this type.

SUMMARY OF THE INVENTION

The subject invention is directed to a new and useful implantable valving device for mechanically regulating blood flow through a blood vessel.

The present invention provides in one aspect an implantable device for regulating blood flow through a blood vessel comprising an elongated support dimensioned and configured to be implanted in a blood vessel and a valve membrane. The support includes axially spaced apart first and second substantially annular support portions and a first linking member linking the axially spaced apart portions to one another. The valve membrane extends between the axially spaced apart support portions and has an upper portion, a lower portion and an intermediate portion. The valve membrane includes a first region and a second lower region wherein the first region is folded over the first linking member for attachment and the second region is adjacent the first region and unattached to the first linking member. The second region is movable between a first position to enable blood flow and a second position to inhibit blood flow.

The device preferably further includes a third region folded over for attachment to the first linking member, wherein the second region is positioned between the first and third region.

In one embodiment, the first linking member is curved and traverses a longitudinal axis of the device. In some embodiments, the support is formed at least in part from a shape memory alloy material and the valve membrane is formed at least in part from ePTFE. Preferably, the valve membrane is coated at least in part with an anti-clotting agent. The support can be integrally formed from a laser cut tube.

The device may further include a second linking member, wherein the valve membrane has a fourth region folded over the second linking member for attachment.

In some embodiments, the upper portion of the valve membrane is attached to a bottom region of the first support portion and the lower portion of the membrane is attached to a top region of the second support portion, wherein a section of the lower portion of the membrane is wrapped around a section of the top region of the support portion.

The present invention also provides an implantable device for regulating blood flow through a blood vessel comprising an elongated support dimensioned and configured to be implanted in a blood vessel and a valve membrane supported by the support and including first, second and third portions. The first portion is attached at a first region of the support, the third portion is attached at a second region of the support, and the second portion is positioned between the first and third portions and unattached to the support. The second portion is movable with respect to the support between a first position to enable blood flow and a second position closer to the support to inhibit blood flow.

Preferably, the first and third portions of the valve membrane form a flap wrapped around a portion of the support, and the second portion forms a flap movable with respect to the first and third portions to create an opening for antegrade blood flow. In a preferred embodiment, the second portion of the valve membrane is closer to a top region than a bottom region of the valve membrane.

The valve membrane may further comprise a fourth portion separate from the second portion and unattached to the support, the fourth portion movable with respect to the support between a first position to enable blood flow and a second position to inhibit blood flow.

In one embodiment, the support includes first and second linking members extending between first and second annular portions of the support, and the second portion forms a first flap adjacent the first linking member and the fourth portion forms a second flap adjacent the second linking member, the flaps each creating a space between the flap and the respective linking member during antegrade blood flow to enable blood flow through the space and the flap closing the space during retrograde blood flow.

The present invention also provides an implantable device for regulating blood flow through a blood vessel comprising an elongated support dimensioned and configured to be implanted in a blood vessel and engagable with a blood vessel wall and a valve membrane. The support includes axially spaced apart first and second support portions and a first linking member linking the axially spaced apart portions to one another. The valve membrane is attached to the linking member, the valve membrane having an upper portion attached to a first section of the support and a lower portion attached to a second section of the support. The valve membrane has an enabling condition to enable blood flow when blood flows in one direction and an inhibiting condition to inhibit blood flow when blood flows in an opposite direction. The upper attached portion of the membrane and the lower attached portion of the membrane remain substantially fixed in position in both the enabling condition and the inhibiting condition and the lower and upper attached portions remain adjacent opposing regions of the vessel wall in both conditions.

The valve membrane preferably includes an intermediate portion between the upper and lower attached portions and a first flap in the intermediate portion, the first flap unattached to the support and movable for creating the flow inhibiting and flow enabling conditions while the upper and lower attached portions remain fixed.

The present invention also provides an implantable device for regulating blood flow through a blood vessel comprising an elongated support dimensioned and configured to be implanted in a blood vessel and a valve membrane supported by the support and having a first condition to enable blood flow and a second condition to inhibit blood flow. The valve membrane is positioned in the vessel at a first angle extending across the vessel to traverse a longitudinal axis of the vessel such that opposite ends of the membrane are adjacent opposing walls of the vessel, and the membrane remains substantially at the first angle in the first and second conditions.

Preferably the valve membrane has a first region unattached to the support formed by at least one cut in the membrane and creating an opening adjacent the support during antegrade blood flow. Preferably, the first unattached region moves adjacent the support to close the opening during retrograde blood flow.

In a preferred embodiment, the valve membrane has a second region unattached to the support and spaced from the first region, the second unattached region formed by at least one cut in the membrane and creating an opening adjacent the support during antegrade blood flow. In this embodiment, the second unattached region moves adjacent the support to close the opening during retrograde blood flow.

In one embodiment, the valve membrane has an upper region and a lower region, and the first unattached region and second unattached region are closer to the top region than the bottom region.

BRIEF DESCRIPTION OF THE DRAWINGS

So that those skilled in the art to which the subject invention appertains will readily understand how to make and use the apparatus of subject invention without undue experimentation, preferred embodiments thereof will be described in detail hereinbelow with reference to certain figures, wherein:

FIG. 1 is a perspective view of the flow regulating device of the present invention, prior to full assembly;

FIG. 2 is a perspective view of the support of the flow-regulating device of FIG. 1;

FIG. 3 is a side perspective view of the flow regulating device illustrating how the membrane is attached to the frame;

FIG. 4 is a front perspective view of the top (distal) portion of the flow regulating device of FIG. 1 showing the membrane in the closed position;

FIG. 5A is a side perspective view showing the membrane in the open position;

FIG. 5B is a side perspective view similar to FIG. 5A showing the membrane in the closed position;

FIG. 6A is a cross-sectional view of the identified area of FIG. 5A showing the membrane in the open position, resulting from antegrade blood flow;

FIG. 6B is a cross-sectional view of the identified area of FIG. 6A showing the membrane in the closed position, resulting from retrograde blood flow;

FIG. 6C is a top view of the upper region of the membrane of FIG. 5B showing the membrane in the closed position;

FIG. 6D is a top view of the upper region of the membrane of FIG. 5A showing the membrane in the open position;

FIG. 6E is a top view of the upper region of an alternate embodiment of the membrane shown in the open position;

FIG. 7 is a view similar to FIG. 4 showing another alternate embodiment of the membrane with flaps forming larger openings for increased antegrade blood flow;

FIG. 7A is a cross-sectional view similar to FIG. 6B except showing the membrane of FIG. 7 in the closed position; and FIG. 8 is a drawing of the anatomy of the patient showing two examples of locations of placement of the flow regulating device.

DETAILED DESCRIPTION OF PREFERRED EMBODIMENTS

Referring now to the drawings wherein like reference numerals identify similar or like components throughout the several views, there is illustrated a flow regulating device constructed in accordance with a preferred embodiment of the subject invention, and designated generally by reference numeral 10. Regulating device 10 includes an elongated support 12 that has upper and lower substantially annular ring portions 14 and 24, each having a series of rounded V-shaped apices 15a facing in an upward direction and a series 15b facing in a downward direction. That is, the upper or distal (with respect to the direction of blood flow) ring portion 14 has a first series of angled struts 13a forming a V and a second series of angled struts 13b forming an inverted V which together form a group of closed substantially diamond shaped cells 19 connected at region 17. Similarly, the lower or proximal (with respect to the direction of blood flow) ring portion 24 has a first series of angled struts 29a and a second series of angled struts 29b, facing in opposite directions and forming closed substantially diamond shaped cells 28 connected at region 27. The cells 28 have upper apices 25 and lower apices 26. For clarity, not all of the identical parts in the drawings are labelled. Note that in the preferred embodiment, the rings and linking member (described below) are preferably integral so that terms "joined", "connected", etc. are used for ease of description.

Support 12 has two curved linking or connecting members 21a, 21b, best shown in FIG. 2 in which the membrane is removed for clarity. The top of each connecting member 21a, 21b extends from a common lower apex 15b of one of the pairs of angled struts 13b of upper ring 14 (see also FIGS. 3 and 4) The lower end of connecting members 21a, 21b extend from separate upper apices 25a, 25b, respectively, of cells 28 of lower ring 24. In the illustrated embodiment, the apices 25*a*, 25*b*, are about 36 degrees apart as ten cells are formed. However, a different number of cells can be provided with different spacing between apices. Also, it should be appreciated that the connecting members can extend from other apices of lower ring 24 or upper ring 14. The connecting members 21*a*, 21*b* have a curve or twist extending close to about 180 degrees (and extending substantially across the vessel when implanted) so that an upper end is connected to one end (viewed radially/transversely) of the device 10 and the lower end is connected to an opposite end (viewed radially/transversely) of the device 10. That is, with ten closed cells in the illustrated embodiment, apex 15*b* is approximately 162 degrees out of phase from apex 25*a* and from apex 25*b*. Other spacing and alternate number of cells is also contemplated.

Although two connecting members are shown, one connecting member or more connecting members could be provided. Also, the connecting members could be spaced further or closer apart and have different curves than shown.

The rings 14, 24 are collapsed to a reduced diameter (profile) position for delivery. The rings 14, 24, when implanted, are substantially perpendicular to the direction of blood flow. Preferably, the rings 14, 16 in their expanded (deployed) configuration are larger in diameter than the internal diameter of the target vessel to apply a sufficient radial force against the vessel to ensure that the device remains in a desired position and orientation after implantation. For example, for use in an 8 mm vessel, the rings could have an expanded outer diameter of about 10 mm and preferably could be collapsed sufficiently to be delivered through a 12 Fr (4 mm) delivery catheter. Others ring diameters are also contemplated.

The support 12 is preferably composed of shape memory material, such as Nitinol or Elgiloy, with a shape memorized larger diameter configuration as shown in the drawings. In the illustrated embodiment, the support is laser cut from a tube so that the connecting members and rings are integral. However, it is also contemplated that alternatively the support can be formed from wire(s). Also, it should be appreciated that instead of being integral, separate members could be provided, with separate rings joined by separate linking (connecting) members.

Device 10 includes a valve member or membrane 50 that is operatively associated with support 12 for regulating the flow of blood through a vessel by moving between open and closed positions. Membrane 50 is preferably formed from a sheet of ultra thin membrane material such as a ePTFE material or the like. It is envisioned that the membranes disclosed herein could be bonded or otherwise coated with an anti-clotting or anti-coagulant/anti-thrombogenic agent such as Heparin and/or an anti-proliferative coating, to retard the body's desire to reject the implant. In a preferred embodiment, the membrane is coated with an anti-thrombogenic agent and the frame is coated with an anti-proliferative agent, such as Dexamethasone by way of example.

As shown, valve membrane 50 has an upper portion 52, an intermediate portion 62, and a lower portion 72. With reference to FIG. 3 which illustrates how the membrane 50 is attached to support 12 in manufacture, the top portion 52 has first and second flaps 54, 56 which are folded down over respective connecting members 21*a*, 21*b* and attached to the membrane to secure the upper portion 52 of membrane 50 about the support 12. FIG. 3 illustrates flap 56 already folded in the direction of arrow F4 from its unfolded position shown in phantom. FIG. 3 also illustrates flap 54 in its unfolded position before movement in the direction of arrow F3 in manufacture to its folded position depicted in phantom. Flaps 57 and 59 at the uppermost region of membrane 50 are wrapped around struts 13*b* in the direction of arrows F1, F2, respectively.

With continued reference to FIG. 3, the intermediate portion 62 of membrane 50 has flaps 64, 66 for connection to linking (connecting) members 21*a*, 21*b*, respectively. Flap 64 is shown in a mostly unfolded position to be folded in the direction of arrows F6 to its folded position shown in phantom where it is attached to the membrane 50. Flap 66 is shown in its unfolded position to be folded in the direction of arrows F5 to its folded position depicted in phantom.

Lower portion 72 of membrane 50 has flaps 74 and 76 which are each folded around a separate strut 29*a*. Arrows F8, F7, respectively, illustrate the direction of the fold.

Cuts in the membrane 50 create an unattached flap 84 between upper attached flap 54 and intermediate attached flap 64 and an unattached flap 86 between upper attached flap 56 and intermediate attached flap 66. These unattached flaps 84, 86 are positioned adjacent the respective connecting member 21*a*, 21*b* as shown, but create a respective opening 90, 91 for blood flow between the membrane 50 and connecting members 21*a*, 21*b* as described below. Note, alternatively, the flaps 84, 86 can extend over the connecting member, as long as it remains unattached and creates a sufficient space from the linking member to create a sufficiently sized opening to allow blood flow therethrough.

Note that FIG. 1 shows the membrane 50 with the flaps open, prior to connection in manufacture, to illustrate how it is wrapped around the support 12 and connected to other portions of the membrane for securement/attachment of the membrane to the support 12. The flaps, after wrapping over/around the region of support 12, can be connected to the membrane body by welding, adhesive, suturing or other methods. Also, an intermediary material can be used to facilitate welding, such as polyurethane or polycarbonate/polyurethane impregnated or otherwise combined with the ePTFE material. It is also contemplated that the membrane can be attached to the support 12 itself by methods such as by adhesive or use of suture material.

As can be appreciated, the body portion of the membrane 50 extends substantially if not entirely across the expanse of the vessel in the open position. However, the openings 90 and 91 adjacent the unattached flaps 84, 86 provide a sufficient gap for the necessary amount of blood flow, it being appreciated by applicants that a normally functioning valve is only open about 35%. In some embodiments, the openings in the membrane created by the space between flaps 84, 86 and the support create a space gap in the range of about 5% to about 15% of the diameter of the vessel. In the alternate embodiment depicted in FIG. 7, larger openings 90' and 91' are formed to allow more antegrade blood flow. In these large opening embodiments, a space (opening) can be created preferably representing about 15% to about 45%, and more preferably from about 15% to about 30% of the diameter of the vessel. (In all other respects the regulating device of FIG. 7 is identical to that of FIG. 4 and the corresponding parts are labelled by numerals with a prime designation and therefore are not discussed herein). These percentages are defined in terms of the diameter of the blood vessel. For example, if a rectangular opening is formed of dimension of 2 mm×4 mm, and is placed in a 10 mm vessel, the cross section occupied by the two openings (about 16 mm) would be about 20% of the overall diameter of the vessel (about 78 mm). It should be appreciated that the foregoing ranges and percentages are provided by way of example and other size openings creating a different percentage opening are also contemplated. Also, other shape openings can be provided other than rectangular, including square, semicircular, etc. FIG. 6E shows by way of example substantially semicircular openings 90", 91" formed by flaps 84". 86", respectively.

Movement of the membrane 50 between an open (blood flow enabling) position/condition to allow antegrade blood flow and a closed (blood flow inhibiting position/condition) to essentially block flow are shown in respective FIGS. 5A and 5B, and shown in more detail in FIGS. 6A-6D. In the closed position, however, a minimal amount of blood flow is allowed as will be discussed below.

More specifically, and with reference to FIG. 5A, blood flowing through the blood vessel V in the downstream direction (antegrade flow) indicated by arrow "D" will act against the valve membrane 50 in such a manner as to push the body portion upwardly as viewed in the drawing, creating a concave belly on the underside. The blood will travel along the concave surface and up the membrane and the blood pressure will force the flaps 84 and 86 upwardly, separating (spreading) them from the respective connecting members 21a, 21b as also shown in FIGS. 6A and 6D to form an opening or gap.

After the pulsed blood travels in the direction of arrow D1 (FIG. 5A), through the openings (spaces) 90, 91, the blood backs up in the direction of arrow C of FIG. 5B. This retrograde blood flow will act against the angled body of the membrane 50, forcing it downwardly as viewed in FIG. 5B to form a convexity on its underside. This downward pressure will force flaps 84, 86 downwardly adjacent to the connecting members 21a, 21b, respectively, and against the connecting member as shown for example in FIG. 6B and 6C, thus essentially closing the openings 90, 91 to prevent blood flow therethrough. However, a small amount of blood will force its way between the membrane 50 and the vessel wall as depicted by arrow C1 in FIG. 5B, thereby reducing stasis or stagnation that could lead to clotting. In embodiments wherein a larger flap is utilized to create a larger opening, such as in the embodiment of FIG. 7, the flap 84' (and 86', not shown) in the closed position would lie adjacent the connecting members, and extend underneath the connecting member (e.g. connecting member 21a') to lie against the vessel wall as shown in FIG. 7A, thereby inhibiting blood flow.

It should be appreciated that the membrane extends at an angle across the vessel of about 50 to about 70 degrees to help direct the blood flow and continuously wash the membrane body to prevent blood stagnation. (Other angles are also contemplated) More specifically, blood contacting the body portion of the membrane 50 in the open position will be directed upwardly, along the concave surface, thereby washing the membrane body to wash away clots to reduce the likelihood of clotting. In the closed position, blood contacting the membrane body will be directed downwardly along the angled body to wash the opposing side of the membrane to likewise reduce the likelihood of clotting.

As can be appreciated, the membrane 50 remains at substantially the same angle across the blood vessel in the open (flow allowing) and closed (flow inhibiting) positions/conditions. That is, as shown in FIGS. 5A and 5B, the upper region of the membrane 50 is adjacent one side of the vessel wall in the open (flow allowing) position The upper region remains adjacent the same wall in the closed (flow inhibiting) position. Similarly, the lower region of the membrane 50 is adjacent an opposite side of the vessel wall, and remains adjacent that wall in both the open and closed positions of FIGS. 5A, 5B, respectively. Thus, the upper and lower attached regions of the membrane remain in substantially the same position.

One example of the location of placement of the flow regulating device in a patient's leg is shown in FIG. 8 with areas A1 and A2 showing possible placement sites of the device, e.g. upstream or downstream of the native valve V.

If composed of shape memory, the device will automatically expand to the position shown either upon release from a delivery member or in response to temperature change. However, if composed of other materials, the device can be designed to automatically expand due to the springiness of the material or can alternatively be implanted in a blood vessel using a balloon catheter (not shown) as described in copending U.S. patent application Ser. No. 11,801,691, the entire contents of which are incorporated herein by reference. That is, rings 14 and 24 can be moved from a closed position to an expanded position by inflating the balloon or by use of a mechanical expander. Upon expansion, the rings 14 and 24 apply a force against the vessel wall, thereby being retained therein. The balloon or mechanical expander is then deflated and the catheter is removed from the blood vessel so the device 10 can regulate the flow of blood through the vessel in the manner described above.

In the embodiments disclosed herein showing substantially circular rings, it should be understood that the rings can be shaped to have a size larger than the diameter of the vessel and therefore, depending on the size of the vessel, may not assume a circular shape but have an oval shape pressing against the vessel wall toward a circular configuration.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure.

What is claimed is:

1. An implantable device for regulating blood flow through a blood vessel, comprising:
    a) an elongated support dimensioned and configured to be implanted in a blood vessel, the support including axially spaced-apart first and second substantially annular ring portions and a first linking member, the annular ring portions circumscribing a longitudinal axis of the elongated support, the first linking member coupled to the first annular ring portion at a first end and coupled to the second annular ring portion at a second end, the first and second ends are substantially opposing each other such that the first linking member traverses the longitudinal axis of the elongated support; and
    b) a valve membrane extending between the axially spaced-apart annular ring portions and having an upper portion, a lower portion and an intermediate portion, the valve membrane including a first region and a second lower region, the first region folded over the first linking member for attachment and the second region being adjacent the first region and unattached to the first linking member, the second region movable between a first position to enable blood flow and a second position to inhibit blood flow.

2. The device of claim 1, further comprising a third region folded over for attachment to the first linking member, the second region positioned between the first and third region.

3. The implantable device as recited in claim 1, wherein the first linking member is curved.

4. The implantable device as recited in claim 1, wherein the support is formed at least in part from a shape memory alloy material.

5. The implantable device as recited in claim 1, wherein the valve membrane is formed at least in part from ePTFE.

6. The implantable device as recited in claim 1, wherein the valve membrane is coated at least in part with an anti-clotting agent.

7. The implantable device as recited in claim 1, further comprising a second linking member, the valve membrane having a fourth region folded over the second linking member for attachment.

8. The implantable device as recited in claim 1, wherein the upper portion of the valve membrane is attached to a bottom region of the first annular ring portion and the lower portion of the membrane is attached to a top region of the second annular ring portion.

9. The implantable device of claim 8, wherein a section of the lower portion of the membrane is wrapped around a section of the top region of the second annular ring portion.

10. The implantable device as recited in claim 1, wherein the support is integrally formed from a laser cut tube.

11. An implantable device for regulating blood flow through a blood vessel, comprising:
  a) an elongated support dimensioned and configured to be implanted in a blood vessel, the support including axially spaced-apart first and second ring members and a first linking member, the ring members circumscribing a longitudinal axis of the elongated support, the first linking member coupled to the first ring member at a first end and coupled to the second ring member at a second end, the first and second ends are substantially opposing each other such that the first linking member traverses the longitudinal axis of the elongated support; and
  b) a valve membrane supported by the support and including first, second and third portions, the first portion attached at a first region of the support, the third portion attached at a second region of the support, and the second portion positioned between the first and third portions and unattached to the support, the second portion movable with respect to the support between a first position to enable blood flow and a second position closer to the support to inhibit blood flow.

12. The implantable device of claim 11, wherein the first and third portions of the valve membrane form a flap wrapped around a portion of the support, and the second portion forms a flap movable with respect to the first and third portions to create an opening for antegrade blood flow.

13. The implantable device of claim 12, wherein the second portion of the valve membrane is closer to a top region than a bottom region of the valve membrane.

14. The implantable device of claim 11, wherein the valve membrane further comprises a fourth portion separate from the second portion and unattached to the support, the fourth portion movable with respect to the support between a first position to enable blood flow and a second position to inhibit blood flow.

15. The implantable device of claim 14, wherein the support includes a second linking traversing the longitudinal axis of the elongated support, wherein the second portion of the membrane forms a first flap adjacent the first linking member and the fourth portion forms a second flap adjacent the second linking member, the flaps each creating a space between the flap and the respective linking member during antegrade blood flow to enable blood flow through the space and the flap closing the space during retrograde blood flow.

16. The implantable device for regulating blood flow through a blood vessel, comprising:
  a) an elongated support dimensioned and configured to be implanted in a blood vessel and engagable with a blood vessel wall, the support including axially spaced-apart first and second ring portions and a first linking member, the ring portions circumscribe a longitudinal axis of the elongated support, the first linking member coupled to the first ring portion at a first end and coupled to the second ring portion at a second end, the first and second ends are substantially opposing each other such that the first linking member traverses the longitudinal axis of the elongated support; and
  b) a valve membrane attached to the first linking member, the valve membrane having an upper portion attached to a first section of the support and a lower portion attached to a second section of the support, the valve membrane having an enabling condition to enable blood flow when blood flows in one direction and an inhibiting condition to inhibit blood flow when blood flows in an opposite direction, the upper attached portion of the membrane and the lower attached portion of the membrane remaining substantially fixed in position in both the enabling condition and the inhibiting condition and the lower and upper attached portions remaining adjacent opposing regions of the vessel wall in both conditions.

17. The implantable device of claim 16, wherein the valve membrane includes an intermediate portion between the upper and lower attached portions, and further includes a first flap in the intermediate portion, the first flap unattached to the support and movable for creating the flow inhibiting and flow enabling conditions while the upper and lower attached portions remain substantially fixed in position.

18. An implantable device for regulating blood flow through a blood vessel, comprising:
  an elongated support dimensioned and configured to be implanted in a blood vessel, the elongated support comprising axially spaced-apart first and second ring members that circumscribe a longitudinal axis of the elongated support; and
  a valve membrane supported by the support and having a first condition to enable blood flow and a second condition to inhibit blood flow, the valve membrane positioned within the elongated support at a first angle extending from the first ring member at a first position to the second ring member at a second position, which opposes the first position, such that the valve membrane traverses the longitudinal axis of the elongated support, the valve membrane remaining substantially at the first angle in the first and second conditions.

19. The implantable device of claim 18, wherein the valve membrane has a first region unattached to the support, the first unattached region formed by at least one cut in the membrane, the first unattached region creating an opening adjacent the support during antegrade blood flow.

20. The implantable device of claim 19, wherein the first unattached region moves adjacent the support to close the opening during retrograde blood flow.

21. The implantable device of claim 18, wherein the valve membrane has a second region unattached to the support and spaced from the first region, the second unattached region formed by at least one cut in the membrane, the second unattached region creating an opening adjacent the support during antegrade blood flow, wherein the second unattached region moves adjacent the support to close the opening adjacent the support during retrograde blood flow.

22. The implantable device of claim 21, wherein the first and second openings create a cross sectional shape ranging from about 15% to about 30% of the diameter of the vessel.

23. The implantable device of claim 21, wherein the valve membrane has an upper region and a lower region, and the first unattached region is closer to the top region than the bottom region.

24. The implantable device of claim 23, wherein the second unattached region is closer to the top region than the bottom region.

\* \* \* \* \*